United States Patent
Birkett et al.

(10) Patent No.: US 7,062,251 B2
(45) Date of Patent: Jun. 13, 2006

(54) MANAGING CRITICAL CARE PHYSIOLOGIC DATA USING DATA SYNTHESIS TECHNOLOGY (DST)

(75) Inventors: Kevin R. Birkett, Gainesville, FL (US); Tony C. Carnes, Gainesville, FL (US); Samuel W. Coons, III, Gainesville, FL (US); Willa H. Drummond, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 109 days.

(21) Appl. No.: 10/794,639

(22) Filed: Mar. 5, 2004

(65) Prior Publication Data

US 2004/0176983 A1    Sep. 9, 2004

Related U.S. Application Data

(60) Provisional application No. 60/452,271, filed on Mar. 5, 2003.

(51) Int. Cl.
*A61B 5/00* (2006.01)

(52) U.S. Cl. .................................. 455/400; 600/483
(58) Field of Classification Search ............... 600/300, 600/323, 301, 483
See application file for complete search history.

(56) References Cited

U.S. PATENT DOCUMENTS

| 5,579,775 A | * | 12/1996 | Dempsey et al. | ........... 600/483 |
| 6,493,568 B1 | * | 12/2002 | Bell et al. | ................... 600/323 |
| 2001/0044823 A1 | * | 11/2001 | Labounty et al. | ........... 709/203 |

* cited by examiner

*Primary Examiner*—Erika A. Gary
(74) *Attorney, Agent, or Firm*—Akerman Senterfitt

(57) ABSTRACT

A method of integrating physiologic data including receiving physiologic treatment data from at least two bedside machines and converting the physiologic treatment data into a machine independent format. The physiologic treatment data can be presented in perceptual real-time. For example, physiologic treatment data from multiple sources can be simultaneously presented within a single graphical user interface. The graphical user interface can be interactive so that displayed graphs can be replotted and timelines revised responsive to user input, such as a point-and-drag motion.

18 Claims, 7 Drawing Sheets

PHYSIOLOGICAL DATA INTEGRATION SYSTEM — 300

Date   F Name   Bed #   Height
Time   L Name   Contact Name:   Weight
Unit   Patient ID     Sex

— 315
— 320

Flowsheet Data

● Patient
○ Family
○ Fluids
○ Growth
○ Other

Flowsheet Interval:
15 Minutes

Patient Information

Patient ID   First Name:
Last Name   Race:
Blood Type   Rh:   Gender:
Birth Date:   Room/Bed #
Unit:   Birth Lenght
Birth Weight:   Mother's F Name:
Mother's L Name:
Mothers B Type:   Rh:

[Comments]   [New] [Discharge] [Save] [Cancel]

Touch Keyboard

```
` 1 2 3 4 5 6 7 8 9 0 - = Backspace
Tab q w e r t y u i o p [ ] \
Caps a s d f g h j k l ; ' Enter
Shift z x c v b n , . / Shift
```
— 325

305 —
310 —

[Machine]
[Lab]
[Trends]
[Reports]
[Flowsheet]

[Setup]
[Keyboard]
[Stylus]

| PHYSIOLOGICAL DATA INTEGRATION SYSTEM | | | [?][X] |
|---|---|---|---|
| Date<br>Time<br>Unit | F Name<br>L Name<br>Patient ID | Bed #<br>Contact Name: | Height<br>Weight<br>Sex |
| Babylog 8000<br><br>CPAP:<br>PIP:<br>FIO2<br>IE ratio:<br>Mean Pres:<br>Flow Rt Set: | Horizon 2000<br><br>Heart Rate:<br>Sys BP:<br>Dia BP:<br>Mean ABP:<br>Spon Resp Rt: | | Machine Data<br><br>■ Babylog 8000<br>■ Horizon 2000<br>☐ N 200<br>■ N395<br>■ Flo-Gard 1<br>■ Flo-Gard 2<br>■ Colleague IP<br>☐ Show All — 515 |
| N 395<br><br>Pulse Amp:<br>Pulse Rate:<br>O2 Sat: | Flo-Gard 1<br><br>Label:<br>Dose Mode<br>Pri Vol Inf:<br>Rate<br>Time Remain:<br>Vol Remain: | | |
| Flo-Gard 2<br><br>Label:<br>Dose Mode<br>Pri Vol Inf:<br>Rate<br>Time Remain:<br>Vol Remain: | Colleague IP<br><br>Label:<br>Dose Mode<br>Pri Vol Inf:<br>Rate<br>Time Remain:<br>Vol Remain: | | |

[Machine] [Lab] [Trends] [Reports] [Flowsheet] [Setup] [Keyboard] [Stylus] — 520

(Figure 6 shows a rotated screenshot labeled "Flowsheet Setup" (600) from a Physiological Data Integration System, with fields including Date, Time, Unit, F Name, L Name, Patient ID, Bed #, Contact Name, Height, Weight, Sex. Navigation buttons: Machine, Lab, Trends, Reports, Flowsheet, Setup, Keyboard, Stylus. A Unit list (605) contains NICU, NICU 2, CICU, MICU, PICU. Defined Data (610) lists Apgar 1, Apgar 2, Birth Length, Birth Weight, Fluid Output. Buttons: Comments, New, Remove, Save, Cancel. Setup panel with Data Collection options: ● Flowsheet, ○ Bedside, ○ Lab, ○ Trend, ○ Report; System Config: ○ System. A Touch Keyboard is shown at bottom.)

FIG. 7

PHYSIOLOGICAL DATA INTEGRATION SYSTEM — 700

Date / Time / Unit
F Name / L Name / Patient ID
Bed # / Contact Name:
Height / Weight / Sex

Trend Setup

- Select a Machine
- Infusion Pumps
- Colleague IP

Available Trends:
- Dose Mode
- Dose Value
- Flow Check
- PBck Vol Inf
- Rate

— 705

Displayed Trends:
- Time Remain
- Rate
- Flow Check
- Dose Mode

Buttons: Comments | New | Remove | Save | Cancel

Touch Keyboard
```
` 1 2 3 4 5 6 7 8 9 0 - = Backspace
Tab q w e r t y u i o p [ ] \
Caps a s d f g h j k l ; '  Enter
Shift z x c v b n , . /  Shift
```

Left sidebar: Machine | Lab | Trends | Reports | Flowsheet
Bottom left: Setup | Keyboard | Stylus

Setup

Data Collection
- ○ Flowsheet
- ○ Bedside
- ○ Lab
- ● Trend
- ○ Report

System Config
- ○ System

MANAGING CRITICAL CARE PHYSIOLOGIC DATA USING DATA SYNTHESIS TECHNOLOGY (DST)

CROSS-REFERENCE TO RELATED APPLICATIONS

This application claims the benefit of U.S. Provisional Application No. 60/452,271, filed in the United States Patent and Trademark Office on Mar. 5, 2003, the entirety of which is incorporated herein by reference.

BACKGROUND OF THE INVENTION

1. Technical Field

The present invention relates to the field of health care and, more particularly, to health care computer information systems that manage physiologic and treatment data.

2. Description of the Related Art

Most health care facilities, such as intensive care units (ICUs), acquire bedside patient information using pen and paper methodologies, such as flowsheets and patient charts. A flowsheet is a spreadsheet-type data matrix representing clinical observations over time. The paper documents used by health care facilities can include patient physiologic data, dates and times that the physiologic data was recorded, patient medications, symptoms, treatments, and clinical observations. For example, patient status information is periodically detected by bedside machines and recorded onto flowsheets by staff for a treating physician to later examine. Portions of these flowsheets can be manually entered into information systems to preserve patient information for administrative and research purposes. Further, paper documents containing physiologic data may require storage for a predefined period for record keeping purposes. Appreciably, the practice of recording and storing physiologic data on paper can be very time-consuming and expensive. Additionally, transcription errors can occur when using paper methodologies, which can result in improper treatment.

These shortcomings in managing physiologic data can be highly problematic. Physician decisions concerning patient treatments can be dependant upon the physiologic data available to the physician. The environment in which the physician works is complex, fast-paced, and is often crowded with both people and devices. Physicians can be summoned from one task to another, more urgent one, in seconds and can occasionally be required to rapidly analyze and treat patients with which the physician is only minimally familiar. In such situations, even the most accurate physiologic data can be useless to a physician if the physiologic data is presented in a confusing manner that takes concentration and time to find and comprehend. If patient data is inaccurate or misinterpreted, improper decisions can be made that can result in life altering consequences. Accordingly, the patient data upon which decisions are based should be presented in a clear, consistent, and comprehensible fashion. Further, the patient data should be available and accessible at the treatments or decision making location in order to be of use.

Another problem that exists with the conventional handling of physiologic data relates to clinical research. In order for clinical researchers to gather physiologic data, the researchers must acquire the paper documents upon which the physiologic data of patients has been recorded. The paper documents can include patient charts and flowsheets. Data from these paper documents can then be manually entered into a computing device so that the physiologic data contained within can be analyzed. This manual data entry process consumes substantial human resources and increases the likelihood of typographical errors. Further, clinical researchers will often be unaware of potentially valuable cases, since the only information sources for these cases can be paper documents, which may be difficult to search. Moreover, the paper documents from which data entry is conducted can contain confidential and/or sensitive patient information. This sensitive information can either limit the physiologic data available for clinical research purposes and/or induce additional data entry difficulties, such as requiring data entry to occur within a secure location.

One reason pen and paper methodologies have been conventionally used for recording physiologic data can relate to data integration difficulties. Presently, most physiologic data is recorded from bedside machines that monitor patients. These bedside machines generally lack the interfaces, such as an Ethernet or other network port, and/or communication standards, such a TCP/IP (Transmission Control Protocol/Internet Protocol) through which networking occurs. The only data port typically included with a bedside machine is a serial or parallel port, such as an RS-232 port. While such a data port can receive and accept data streams, these data streams follow no open standards, i.e. each bedside machine can transmit data in a proprietary manner using different data formats and protocols. In order for a computing device to communicate with a bedside machine via a data port, a tailored application must be uniquely written for that particular type of bedside machine. Present bedside machines are not packaged with software applications that facilitate communication via the data port.

A few systems do exist which can centrally present physiologic data gathered from multiple sources. These systems, however, typically exchange information in a propriety manner and can only communicate with other bedside machines which use the same proprietary protocol, i.e. other machines from a particular product line of a common manufacturer. Physiologic data from sources external to these proprietary monitoring systems, i.e. other manufacturer's bedside machines, cannot be integrated with the data contained within the proprietary monitoring systems. For example, the same type of bedside machine(e.g. a ventilator) made by a different manufacturer than the manufacturer of the proprietary monitoring system cannot be integrated with the proprietary system. Consequently, to achieve even the minimal data sharing capabilities provided by these proprietary networks, a health care provider is "locked into" a single bedside machine series or a single product line of a manufacturer. One effect of this lock-in can be a lack of a competitive marketplace resulting in higher costs and fewer monitoring options.

Presently, some systems are available to acquire data from bedside machines, however, these systems tend to utilize a proprietary physical connection and do not address unit workflow issues which is a core part to the present invention. Moreover, the presentation mechanisms for physiologic data cannot be configured so that physiologic data is presented in a manner designed to optimize physician comprehension. Further, conventional systems that monitor physiologic data do not provide mechanisms to facilitate data extraction to be used for clinical research.

SUMMARY OF THE INVENTION

The invention disclosed herein utilizes data synthesis technology (DST) to integrate physiologic data from at least one bedside machine with data from other data sources, such as computerized laboratory information systems. More particularly, a bedside computing device can be communicatively linked to at least one bedside machine via a data port, such as a RS-232 port. The bedside computing devices can include device drivers written for the various bedside machines with which the bedside device can communicate. Physiologic data, such as laboratory data, pharmacological data, care facility data, and bedside machine data, can then be presented within the bedside computing device in a configurable fashion within a single interface. The bedside computing device can be communicatively linked to a trusted network including care facility computing resources. The data protocols used by different computing devices and bedside machines can be synchronized to one another and stored into a local database and/or a centralized data repository. Additionally, synchronized data can be filtered for multiple health related purposes. For example, clinical research facilities can access stored patient physiologic data that has been filtered so that patient privacy information and identification has been removed.

One aspect of the present invention can include a method of integrating physiologic data that seamlessly complements the existing workflow process. The method can include receiving physiologic data from at least two bedside machines and converting the physiologic data into a machine independent format that is dynamically matched with discreet workflow data elements. For example, a data stream can be received from each of the bedside machines and a transport protocol particular to one of the bedside machines can be determined for each data stream. Thereafter, the data stream can be segmented into discrete elements. In one embodiment, for each of the discrete elements, a cross reference table can be utilized to determine a standard data format associated with the discrete element. At least a portion of the discrete elements can then be converted into the standard data format. The physiologic data can then be presented. In another embodiment, patient specific information can be removed from the physiologic data for clinical research use. In yet another embodiment, the method can respond to a user-driven request in perceptual real-time. For example, a user can request data and/or trend reports and be quickly presented with the requested data and/or trend reports. Such a data presentation will occur even if the data and/or trend reports relate to real-time physiologic data for presently monitored patients.

Another aspect of the present invention can include a system for integrating physiologic data. The system can include a bedside machine for monitoring physiologic data that includes a data port for serial communication. A bedside computing device can be communicatively linked to the bedside machine through the data port and communicatively linked to a network through a network port. The system can also include a centralized data repository that is communicatively linked to the bedside computing device through the network port, wherein the centralized data repository is configured to synchronize data from a plurality of bedside machines, and wherein at least a portion of the bedside machines utilize different data conventions. An additional physiologic data source, such as a care network information system, a laboratory information system, and/or a pharmacy information system, can also be included. In one embodiment, at least a portion of the data from the bedside machines can be accessed by a clinical research facility after the data is "scrubbed" and replicated to the centralized data repository.

Another aspect of the present invention can include a system for integrating bedside physiologic data including at least two bedside machines, each configured to monitor at least one physiological condition. Each bedside machine can include a data port. A bedside computing device can be configured to present data from the bedside machines. The bedside computing device can include a data port and a network port. Additionally, the bedside computing device can be communicatively linked to the bedside machines through the data ports. In one embodiment, the bedside computing device can include at least one bedside machine driver configured for particular ones of the bedside machines. Each bedside machine driver can facilitate data exchanges between the bedside machines and the bedside computing device. The bedside computing device can also be configured to communicate physiologic data with a data source such as a laboratory information system, a hospital information system, and a pharmacy information system.

BRIEF DESCRIPTION OF THE DRAWINGS

There are shown in the drawings embodiments, which are presently preferred, it being understood, however, that the invention is not limited to the precise arrangements and instrumentalities shown.

FIG. 3 is an exemplary graphical user interface showing flowsheet data for patient information using the system of FIG. 2.

FIG. 5 is an exemplary graphical user interface showing data for multiple bedside machines using the system of FIG. 2.

FIG. 6 is an exemplary graphical user interface for setting up a flowsheet display using the system of FIG. 2.

FIG. 7 is an exemplary graphical user interface for setting up a trend display using the system of FIG. 2.

DETAILED DESCRIPTION OF THE INVENTION

The invention disclosed herein provides a method, system and an apparatus for integrating physiologic data, which can be generically referred to as providing physiologic data using data synthesis technology (DST). More particularly, data streams can be conveyed between bedside machines that monitor physiologic data and a computing device communicatively linked to a network. The computing device can interpret the data streams sent from specified machines and transport the information contained within the data streams to a networked element. This networked element can transform the information into a machine-independent data schema. The information provided by bedside machines and other patient relative information, such as pharmacological data and laboratory results can be integrated within a single presentation device. For example, a bedside computing device can contain physiologic, laboratory, pharmacy, and other patient-centric data for a given patient. Additionally, physiologic data can be analyzed by other health-related systems. For example, clinical research facilities can access stored patient physiologic data that has been sanitized so that patient privacy information and identification has been removed.

As used herein, bedside refers to an environment in close proximately to a patient being treated. Items placed within a bedside environment should be near enough to the patient that a physician treating the patient can access the items while treatment is being performed. It should be noted that a bedside environment need not include a bed. For example, instead of a bed, a patient can be contained within an incubator, an ambulance, a gurney, a cot, an operating table, and the like. The term bedside should be liberally construed. For example, an apparatus which monitors conditions within the bedside environment, yet which is at least partially disposed outside the environment around the patient can, nevertheless, be considered a bedside apparatus. Similarly, an apparatus that can provide information to an individual, such as a physician, located within the bedside environment can be considered bedside apparatus even if necessary portions of the apparatus are in a location remote from the patient.

Figure 1:
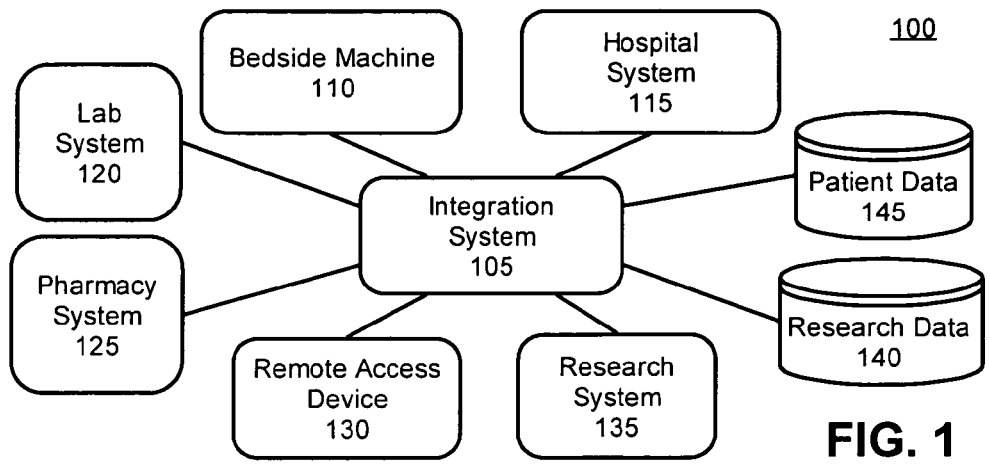
FIG. 1 is a schematic representation of a system for integrating physiologic information in accordance with the inventive arrangements disclosed herein.

FIG. 1 is a schematic representation of a system 100 for integrating physiologic data in accordance with the inventive arrangements disclosed herein. The system 100 can include an integration system 105, a bedside machine 110, a hospital information system 115, a laboratory information system 120, a pharmacy information system 125, a remote access device 130, and a research information system 135. The integration system 105 can receive information, including physiologic information, from multiple sources, transform the information into data elements formatted according to a database schema, and convey these data elements to a variety of customized applications.

The integration system 105 can store all patient information for a particular hospital within one or more data stores, such as research data store 140 and patient data store 145. By using different data stores, privacy considerations can be handled automatically without extensive human intervention and/or costs. Notably, the various data stores of the integration system 105 can include data from a multiplicity of different databases that are continuously or periodically synchronized to one another. Each of these databases can utilize the same or different information structures. When diverse information structures are included within the integration system 105, a data warehouse can help reconcile differences among data elements.

The bedside machine 110 can be a sensor of physiologic data that can determine one or more parameters relating to the health of a patient. The bedside machine 110 can include a blood gas monitor, an infusion pump, a physiological monitor, a pulse oximeter, a flowmeter, a ventilator, an automated patient care bed, a thermocouple probe, and the like. The bedside machine 110 can also include a data port for electronically conveying the physiologic information to connected computing devices. If a data port is not originally included within the bedside machine 110, then one can be retrofitted to the bedside machine 110. The data port can communicate via a physically connected cable or though a wireless transmission means, such as radio frequency. Notably, the bedside machine 110 can be a device integrated within other bedside machines and/or can be a standalone device. The bedside machine 110 can be any one of a plurality of devices that detect physiological parameters for patients, i.e. as typically located in a care taking facility, such as an intensive care unit (ICU). Further, multiple bedside machines 110 that monitor a patient can be connected to the integration system 105. Physiologic data from the multiple monitors can be simultaneously displayed on a single presentation device within the integration system 105.

The hospital information system 115 can be the information system used by a health care provider that contains patient and staff information. The hospital information system 115 can include, but is not limited to, patient medical records, a reference table between treating physicians and patients, patient contact information, physician contact information, and important patient medical annotations, such as allergies, blood type, donor status, and other medical attributes for patients. The hospital information can also contain information concerning employees working specified shifts, on-call physicians, and alternative treating physicians for particular patients.

The laboratory information system 120 can be the information system used by a medical laboratory. The laboratory information system 120 can include information related to conducted tests, such as the date of a test, a patient identifier, a sample identifier, methodologies used, examiner information, test results, and other test annotations. A laboratory information system 120 can be integrated within another information system, such as the hospital information system 115, or can function autonomously. Further, the laboratory information system 120 can be a system limited to a particular laboratory, or can contain information from a multitude of laboratories located at the same or different locations.

The pharmacy information system 125 can be an information system used to record patient prescription information. For example, the pharmacy information system 125 can contain a date for a prescription, prescription strength, prescription dosage, prescribing physician, patient, number of refills, known drug side effects and warnings, and the like. The pharmacy information system 125 can be an integrated system containing information from many different pharmacies or can be restricted to a particular pharmacy, such as one within a hospital or treating facility.

The remote access device 130 can include any device communicatively linked to the integration system 105. For example, the remote access device can be a physician's home computer linked via the Internet to the integration system 105. In another example, the remote access device can be a data tablet wirelessly connected to the integration system 105. Additionally, the remote access device 130 can be a warning mechanism, such as an auditory or visual alarm that can be triggered upon the receipt of a specified signal from the integration system 105.

The research information system 135 can be an information system containing data relating to clinical research involving physiologic data. While the research information system 135 can be dedicated to a single research facility, the research information system 135 can also contain multiple different geographically separated research institutions and/or organizations. For example, the research information system 135 can be a general university system that includes multiple interconnected medical universities located within one or more countries.

Figure 2:
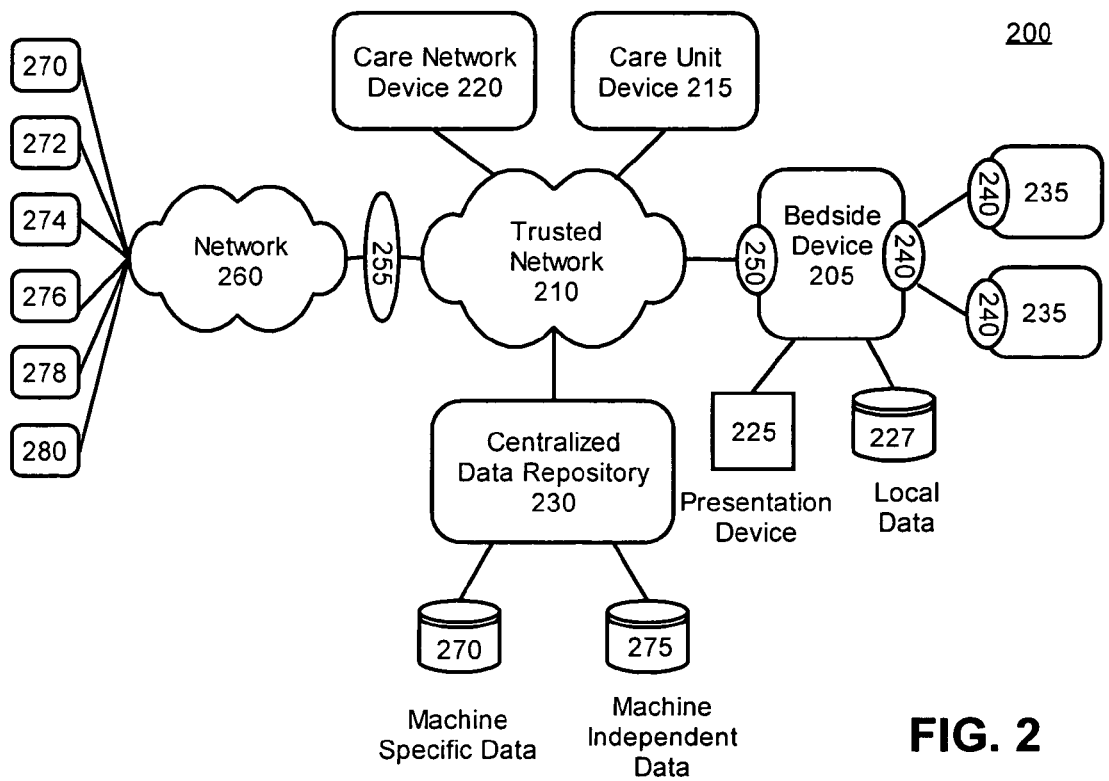
FIG. 2 is a schematic representation of an integration system for integrating physiologic information within the system of FIG. 1.

FIG. 2 is a schematic representation of an integration system 200 for integrating physiologic information used in conjunction with the system of FIG. 1. System 200 can include a bedside device 205, a trusted network 210, a care unit device 215, a care network device 220, a centralized data repository (CDR) 230, and one or more bedside machines 235. The bedside machines 235, which have been previously defined in FIG. 1, can be a sensor of physiologic data that can determine one or more parameters relating to the health of a patient. Each bedside machine can include a data port 240. If the data port 240 is not installed at the time of manufacture, one potentially can be retrofitted for the bedside machine 235. The data ports 240 can convey a data stream between the bedside machine 235 and the bedside device 205. The data port 240 can include any serial or parallel connection such as FireWire, USB (Universal Serial Bus), Centronics, an infra-red port, and the like. For example, the data port 240 can be an RS-232 connector that can convey information as a serial data stream.

The bedside device 205 can be a computing device capable of managing and presenting physiologic data at a bedside location. For example, the bedside device 205 can be a computer that accesses and organizes patient data. Alternately, the bedside device can be a communication portal that reconciles data streams between local equipment and a network. Multiple bedside devices 205 can be utilized within system 200, where each bedside device 205 can manage data for one or more patient beds. The bedside device 205 can handle a variety of different peripheral devices. These peripheral devices can include one or more bedside machines 235, a local data store 227 and a presentation device 255. Further, the bedside device 205 can include a data port 240 that is compatible with the data port 240 of the bedside machine 235. The bedside device 205 can also include device drivers to convert received data streams to a format independent of any particular bedside machine 235.

The local data store 227 can be any type of information storage device compatible with the bedside device 205, such as magnetic, optical, and/or electronic storage devices. By storing data locally within the local data store 227, the system 200 can provide integrated data even when network difficulties prevent the bedside device 205 from accessing the trusted network 210. The local data store 227 can store 'raw' data from the bedside machine 235, as well as data from other information sources connected to the trusted network 210. The presentation device 255 can be any device capable of presenting data stored within the local data store 227 to a user. The presentation device 255 can include, but is not limited to, a computer monitor, a touch screen, a printer, a fax machine, and/or an audio output device. The bedside device 205 can communicate to the trusted network 210 via a network gateway 250.

The bedside device 205 can also contain a driver for each different bedside machine 235 connected thereto. This driver can be used to translate the data stream into content that can be relayed across a network. Each driver can have knowledge of a corresponding type of bedside machine 235. The device driver can interpret device specific protocols for data streams of the bedside machine 235. Additionally, different drivers can be used to interpret data streams sent from different bedside machines 235.

The trusted network 210 can be an intranet including communicatively linked caregiver computing assets. Some of the devices within the trusted network can be isolated from other communicatively linked devices using network firewalls 255. Within the trusted network 210, physical and logical security precautions can be taken to impede unauthorized information access. A few of the caregiver computing assets that the trusted network 210 can link include the bedside device 205, the care unit device 215, the care network device 220, the CDR 230, and one or more other networks 260.

The care unit device 215 can be a computing device that maintains information on a unit level for a health institution. For example, The care unit device 215 can include, bus is not limited to, personnel information for various shifts, bed availability information, an inventory of bedside machines, operating room schedules for a given care unit, and contact information for patients, physicians, and staff. In one embodiment, the care unit device 215 can include physiologic information derived from various bedside devices 205 within a care unit. For example, the care unit device 215 can be located within a unit nursing station and can include summary information for all bedside machines 235 in use within the care unit. Further, the care unit device 215 can provide warnings whenever parameters for a given bedside device exceed predetermined limits. The care unit device 215 can also present reminder information detailing when particular patients require assistance, such as needing fluids replaced, pills dispensed, and/or need sanitary assistance.

The care network device 220 can be the computing device that maintains information on the care giving network level, therein providing inter-unit coordination. The care network device 220 can assure that when patients are transferred from one bedspace or care unit to another, all treatment information is properly transferred. For example, if a patient is moved from one bed to another, the care network device 220 can assure the appropriate information is presented within the bedside device 205 associated with the new bed. Additionally, the care network device 220 can display warnings when the same patient is simultaneously assigned to multiple beds or when a current patient that has not been discharged is not assigned to any bed. Moreover, the care network device 220 can assist in patient management for a hospital, hospital system, or health care network. The care network device 220 can also include summary data for the various units that comprise a heath care network.

The CDR 230 can perform data reconciliation between two or more diverse sources. For example, the CDR 230 can synchronize patient data from a laboratory database with similar information contained within a database of a hospital information system. In another example, the CDR 230 can convert information presented in a machine specific format from one of the bedside machines 235 into a standardized schema. Patient information received by the CDR 230 can be converted to adhere to defined data standards and stored in a machine independent data store 275.

In order to perform these data conversions, tables that cross-reference machine or database specific data to standardized data can be stored within a machine specific data store 270. Each supported data source, such as a particular bedside machine 235, can have appropriate cross reference tables for data conversion stored within the machine specific data store 270. For example, one bedside machine 235 can store pulse rate as a floating-point variable called RATE, while the data standard can record pulse rate as an integer variable called PULSE. In this example, data stored within the machine specific data store 270 can detail that RATE equals PULSE. The CDR 230 can also convert the content within the variables from a floating-point value to an integer. Using the machine specific data store 270 information can be conveyed to and from various sources within the trusted network 210 without concern for data formatting peculiarities.

It should be noted that the CDR 230 can perform real-time and/or near-real-time data conversions. Accordingly, information from the bedside machine 235 can be converted by the CDR 230 to a data standard. The standardized data can be conveyed to the bedside device 205 for display. Performance considerations necessary for real-time conversions can require some of the converting functions normally carried out within the CDR 230 to be performed with the bedside device 205. In such an instance, functions and/or conversion information can be sent to the bedside device 205 from the CDR 230. In one embodiment, each bedside machine 235 can perform the functionality attributed to the CDR 230. In such an embodiment, the bedside machine 235 can monitor and translate present physiologic data from multiple ones of the bedside machines 235 without the assistance of external networked elements.

The trusted network 210 can be communicatively linked to network 260 through gateway 255. Gateway 255 can provide security measures, such as passwords and encryption algorithms, to assure that only authorized parties can access the trusted network 210. Various sources that can access the trusted network 210 can include, but are not limited to, a laboratory 270, a hospital information system 272, a pharmacy information system 274, a researcher 276 or clinical research facility, a doctor 278, and an administrator 280.

In operation, a patient can be monitored by the bedside machine 235 that includes the data port 240. A data stream, such as a byte-level data stream, can be sent from the bedside machine 235 to the bedside device 205. When the data stream is conveyed at the byte-level, the data port 240 can function as an interface between data terminal equipment (the bedside machine 235) and data communication equipment (the bedside device 205), which can employ binary data interchange to convey information. A device driver within the bedside device 205 can facilitate communications with the bedside machine 235.

For example, the bedside machine 235 can be used for monitoring blood pressure. Such a machine can generate a data stream having discrete 20 byte segments, where the first 4 bytes in each byte segment identify the machine, the next 6 bytes contain a timing parameter, the next 5 bytes a systolic value, and the final 5 bytes a diastolic value. The device driver for the bedside machine 235 can correctly interpret the segments data stream for the machine. Notably, a different manufacturer of a different bedside machine 235 for blood pressure monitoring can segment a data stream into 30-byte segments. The different bedside machine 235 can have a different driver associated with it. Both blood pressure machines described can be alternatively used within the system 200.

Once data stream information has been properly segmented, the segmented information can be relayed from the bedside device 205 to the trusted network 210 via the gateway 250. Then, the data from the bedside machine 240 can be converted into a standard format by the CDR 230. The converted information can be copied into the machine independent data store 275 and transferred to the bedside device 205. Information can also be provided by other data sources such as the laboratory 270, the hospital information system 272, and the pharmacy 274. The data from other data sources can be integrated within the bedside device 205. Further integrated information can be accessed externally from remote computing devices. For example, a doctor on-call can access the bedside device 205 information via the Internet, even when that doctor is offsite. This ability can help provide correct and rapid responses to changes in patient health as well as relieve doctors of needless visits. Thus, better care can be provided at less cost to the patient.

FIG. 3 is an exemplary graphical user interface (GUI) 300 for a bedside device of FIG. 2. The GUI 300 can include a patient overview section 305, an application selection section 310, a content selection section 315, a content selection 320, and an input section 325. The patient overview section 305 can include general patient information such as date, unit, name, bed, height, weight, sex, and a patient identifier. In particular embodiments, additional patient background information, such as patient history, can be accessed by clicking an appropriate button located within this section. The information within the patient overview section 305 can be derived from a number of sources including a hospital information system.

The application selection section 310 can allow for the selection of one or more integrated applications. The application selection section 310 can include, but is not limited to, applications for bedside machines, laboratories, trends, reports, and patient flowsheets. In one embodiment, the selection made within the application selection section 310 can be linked to the content selection section 315. In such an embodiment, a selection made within the application selection section 310 can cause different options to appear within the content selection section 315.

In another embodiment, a selection within the application selection section 310 can open a view within which the selected application can appear. This window can be an emulation window showing the content of a networked application. For example, the selection of the machine button within the application selection section 315 can cause a window to appear emulating the screen of a selected machine, such as an infusion pump or a pulse oximeter. Such an emulation screen can be useful for physicians, who are familiar with standard machine readouts, to view patient data, whether the physician is at the bedside or accessing the system from a remote location.

The content selection section 315 can allow one or more selections to be made which determine the content displayed within the content section 320. The content selection section can display a flowsheet interval, such as 15 minutes or another predetermined or selectable time interval, which represents the time frame in which new flowsheet data should be gathered. The flowsheet interval can be selected by the treating physician depending on the needs of the patient.

The content section 320 is the main section of the GUI 300 and can display selected patient information. In GUI 300, the content section 320 presents patient information including, but not limited to, patient identifier, last name, blood type, birth date, unit, mother's name, gender, room, and bed. The patent information displayed within the content section 320 can vary depending on patient age, type, and care unit. For example, the mother's name and blood type can appear within the content information section 320 whenever the patient is a newborn.

The input section 325 can be available whenever the GUI 300 appears within systems with touch screen capabilities or other input means, such as a printing device. Thus, although peripheral keyboards can be used, such devices are not necessary for operation. Alternately, the GUI 300 can appear within a personal data assistant (PDA) communicatively linked to a bedside device. Since a bedside device will commonly be located within a patient's vicinity, touch screens, such as the one depicted in the input section 325, represent one minimally intrusive way to provide an input means for the bedside device. It should be noted that any input device, such as a stylus, an external keyboard, and/or a microphone for speech input, can be included within the invention.

Figure 4:
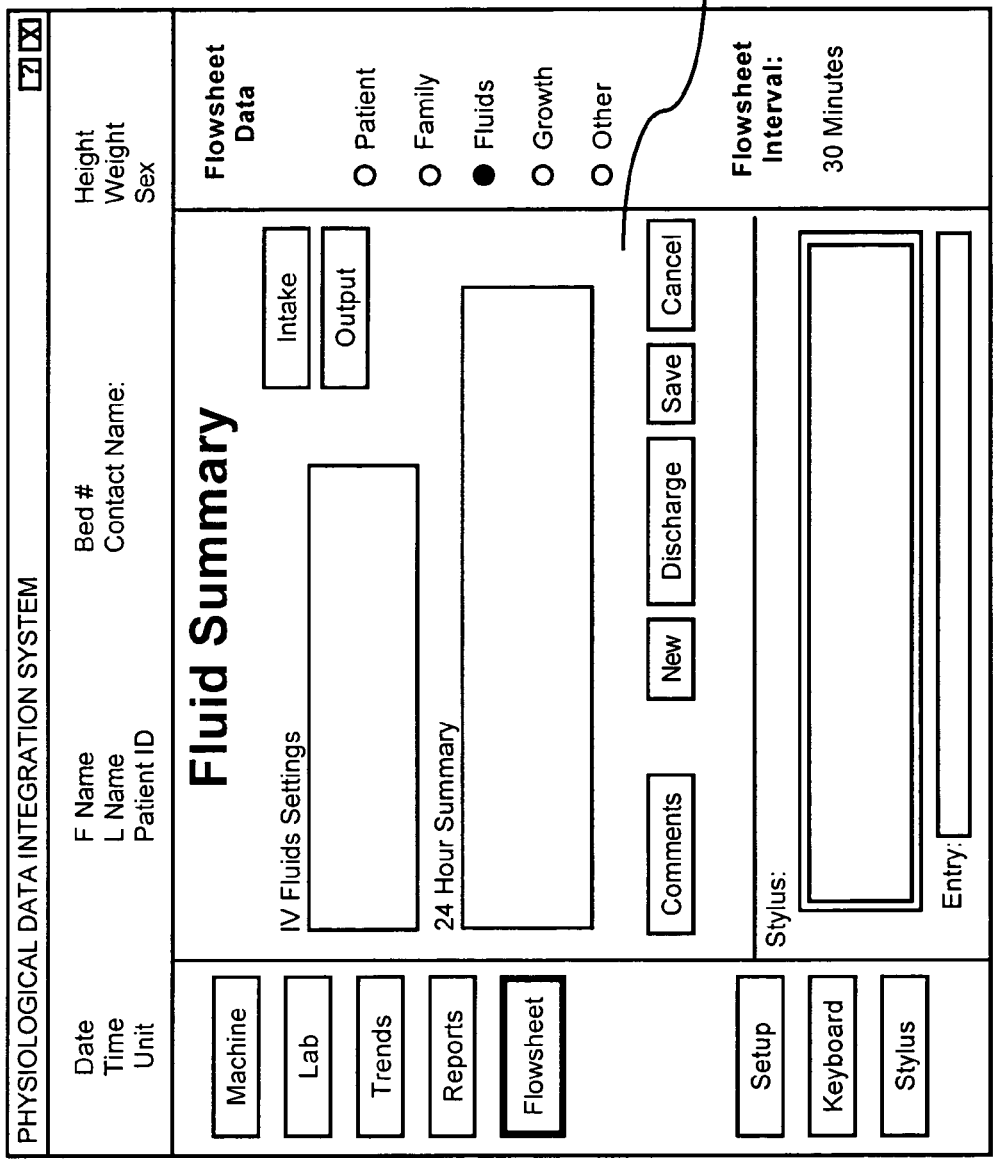
FIG. 4 is an exemplary graphical user interface showing flowsheet data for patient fluids using the system of FIG. 2.

FIG. 4 is an exemplary GUI 400 showing flowsheet data for patient fluids using the system of FIG. 2. The GUI 400 utilizes the same conventions described within FIG. 3 and can, but need not, be used in conjunction with the GUI shown in FIG. 3. The content section 420 of GUI 400 displays summary data for fluids received by a patient. Additionally, clinician notes (not shown), such as particular symptoms to visually check when performing rounds can be included as well. The fluid settings displayed within the fluid summary can be manually entered by treating staff and/or can be automatically entered via a direct communication connection with a fluid controlling bedside machine.

In one embodiment, the GUI 400 can be integrated with a hospital inventory system where patient fluids can contain a bar code. Before a patient is infused with a fluid, the selected fluid can be scanned. If the annotations associated with the scanned fluid do not match physician annotations for treatment, a warning message (not shown) can be displayed by GUI 400. Further, once the fluid is scanned, information within GUI 400, as well as other system information, can be automatically updated. Such an embodiment demonstrates one of many potential advantages and automatic safeguards that can be implemented within a patient care facility where bedside patient care data is integrated among various networked information systems.

FIG. 5 is an exemplary GUI 500 showing data for multiple bedside machines using the system of FIG. 2. The GUI 500 demonstrates that data from more than one bedside machine can be simultaneously displayed. Available beside machines associated with a particular bedside device can appear within the content selection section 515. Check boxes, or other selection criteria, can be provided so that system users can determine what information should appear within the content section 520. If multiple ones of the same bedside machine type are used for a given patient, such as Flo-Gard 1 and Flo-Gard 2 (a Flo-Gard bedside machine being available through Baxter Healthcare Corporation of Deerfield, Ill.), data from both machines can be displayed.

The data displayed within GUI 500 can represent a situation where multiple bedside machines have been connected to a particular patient at different times. For example, in one embodiment, Flo-Gard 1, Flo-Gard 2, and Colleague IP were used on a particular patient that has received fluids. Since the invention can reconcile data differences among differing bedside machines, the same data elements for different machines can be presented within GUI 500. Additionally, the data from the different bedside machines can be easily merged together. Accordingly, although fluids were delivered and measured by three different bedside machines, a single composite graph or chart (not shown) for the patient's fluid intake and status can be automatically created and displayed.

FIG. 6 is an exemplary GUI 600 for configuring a flowsheet display using the system of FIG. 2. GUI 600 illustrates that data from various data collection sources, such as the lab, bedside machines, and user entered flowsheets, data elements can be configured for the needs of a particular patient and/or treating physician. In GUI 600, each unit can have different presentation and data requirements associated with it. Once a unit is selected within selection box 605, a number of defaults can be automatically displayed in defined data box 610. For example, the selection of NICU for unit can cause the display data to contain elements for birth length, fluid output, urine output, and the like. The flowsheet setup can also have an associated flowsheet interval. A default flow sheet interface can be determined based on the bedside machines connected to a particular patient.

FIG. 7 is an exemplary GUI 700 for configuring a trend display using the system of FIG. 2. The GUI 700 allows a user to configure what trends the system should monitor as well as the trends that should be displayed. Different users using different computing devices can be presented with different trend options. For example, a treating physician using a bedside device can be presented with trends for particular patients in scroll box 705. Additionally, a physician can be presented with trends relating to variables within bedside machines that monitor treated patients. For example, trends related to detected physiologic data from different sources can be determined, such as a relationship between a value recorded by a pulse oximeter and a value from a flowmeter.

In another example, a care unit administrator using a care unit device can be presented with trends showing the volume of patients cared for by month and corresponding hardware resource requirements. In yet another example, a hospital facilities administrator can use a care network device to determine maintenance verse operational time for a particular type of bedside machine. Further charts comparing different types of bedside machines can be displayed along with any annotations made by physicians, staff, and maintenance concerning that machine type. Trends and charts from any communicatively connected source can be analyzed by the system.

Figure 8:
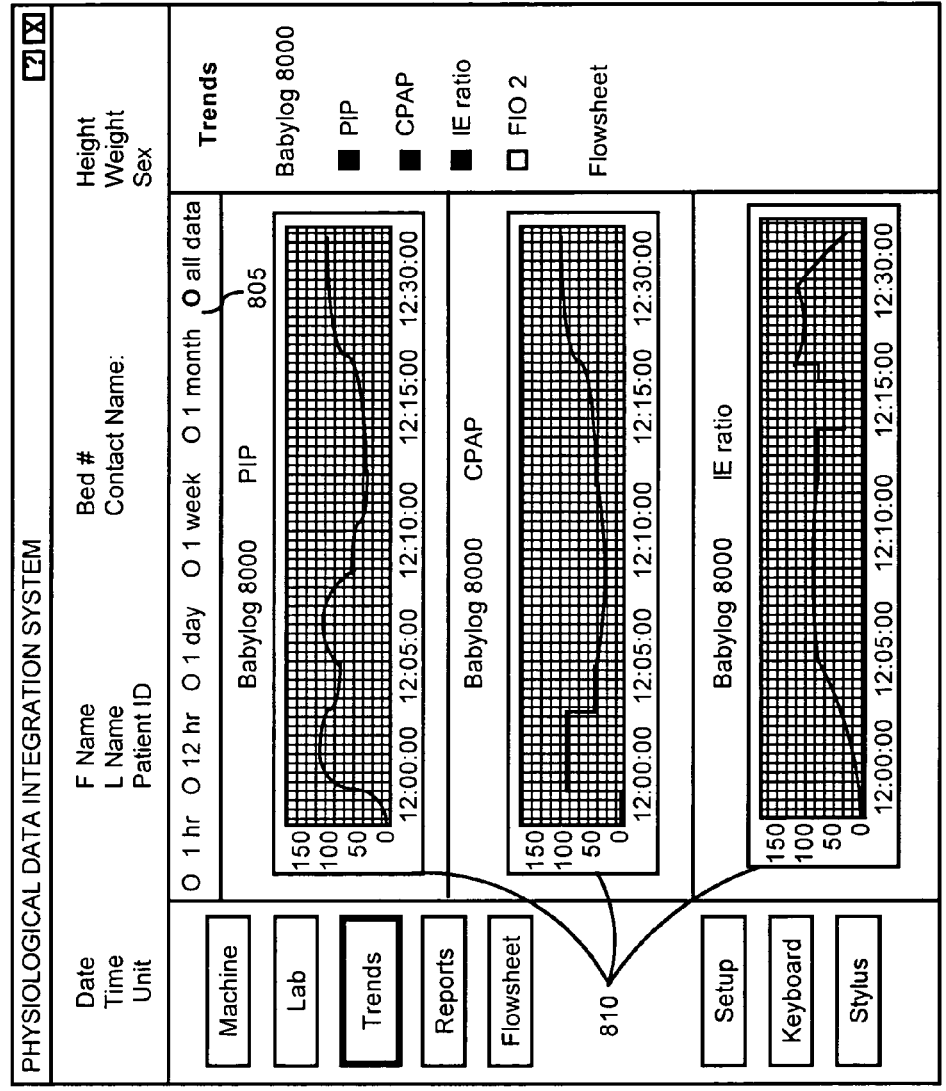
FIG. 8 is an exemplary graphical user interface showing trends using the system of FIG. 2.

FIG. 8 is an exemplary GUI 800 showing trends using the system of FIG. 2. The GUI 800 displays trends for a particular machine type, the Babylog 8000. Values can be selected within the content selection section 805 for display. In the example shown in GUI 800, the peak inspiratory pressure (PIP), continuous positive airway pressure (CPAP), and inspiratory and expiratory times (IE ratio) have been selected for the Babylog 8000. Responsively, graphs showing the selected values verses time can be displayed within the content section 810. Each graph can be displayed according to a selected time frame, such as by the hour, shift, day, week, month, or any other time period. In particular embodiments, treating physicians can set conditions upon monitored trends that cause a message to be responsively displayed upon the occurrence of that condition. For example, if a particular patient's temperature rises above a defined reading, such as 103 degrees Fahrenheit, for longer than a minute, a warning can be generated within the appropriate bedside device and the appropriate care unit device. This ability to add algorithmically determined conditions can supplement warnings generated by particular bedside machines.

It should be appreciated that the GUIs of FIGS. 3 through 8 can be displayed on a variety of different computing devices. Each of these devices can be used conjunctively or alternatively with the various computing devices described within FIG. 2. Further, the computing devices shown in FIG. 2 can use wired or wireless connections for exchanging information between the various computing devices of the system.

For example, in one embodiment the GUIs can be presented within a personal data assistant (PDA) carried by a treating physician. The PDA can contain a networking component, such as a Bluetooth attachment that can convey signals to and from bedside computing devices. The closest bedside device that is within range of the PDA, typically 30 feet, can transmit information to the bedside device. Thus, any comments and/or annotations that the physician made within his/her PDA concerning the patient can be automatically transferred to the bedside device. Additionally, a physician making rounds can retrieve updated information concerning his/her patients to be fully examined at a later time, such as when the physician is called concerning dispositional instructions for a given patient.

In another embodiment, an identification chip can be implanted within a patient's ID bracelet. This identification chip can assure that physician's have the appropriate patient information. For example, if a patient is rushed into an operating room for emergency care, the identification chip can be read and the patient's information displayed within a bedside device of the operating room. Consequently, the invention can be used within a pervasive computing environment to assure that patient data is not confused and that the correct information is always available to treating physicians within a dynamic health care environment.

The various GUIs disclosed herein are shown for purposes of illustration only. Accordingly, the present invention is not limited by the particular GUI or data entry mechanisms contained within views of the GUI. Rather, those skilled in the art will recognize that any of a variety of different GUI types and arrangements of data entry, fields, selectors, and controls can be used to access system 200. Further, the computing devices depicted herein can be functionally and/or physically implemented with other computing devices and the invention should not be limited by the particular exemplary configuration shown.

The present invention can be realized in hardware, software, or a combination of hardware and software. The present invention can be realized in a centralized fashion in one computer system or in a distributed fashion where different elements are spread across several interconnected computer systems. Any kind of computer system or other apparatus adapted for carrying out the methods described herein is suited. A typical combination of hardware and software can be a general-purpose computer system with a computer program that, when being loaded and executed, controls the computer system such that it carries out the methods described herein.

The present invention also can be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

This invention can be embodied in other forms without departing from the spirit or essential attributes thereof. Accordingly, reference should be made to the following claims, rather than to the foregoing specification, as indicating the scope of the invention.

What is claimed is:

1. A method of integrating physiologic treatment data comprising the steps of:
    receiving physiologic treatment data from at least two bedside machines;
    converting said physiologic treatment data from a machine specific format into a machine independent format within a computing device remotely located from said bedside machines;
    performing at least one programmatic action involving said machine-independent data; and
    presenting results from said programmatic actions upon a bedside graphical user interface.

2. The method of claim 1, wherein said convening step further comprises the steps of:
    receiving a data stream from each of said bedside machines;
    for each data stream, determining a transport protocol for said data stream, wherein said transport protocol is particular to said bedside machine; and
    segmenting said data streams into discrete elements.

3. The method of claim 2, further comprising the steps of:
    for each of said discrete elements, referencing a data store to determine a standard data format associated with said discrete element; and
    converting at least a potion of said discrete elements into said standard data format, wherein said presenting step uses said standard data format.

4. The method of claim 1, further comprising the steps of:
    removing patient specific information from said physiologic treatment data; and
    storing said physiologic treatment data for clinical research use.

5. The method of claim 1, further comprising the step of:
    responding to a request from said bedside graphical user interface in perceptual real-time.

6. A system for integrating physiologic treatment data comprising:
    a bedside machine for monitoring physiologic treatment data that includes a data port for serial communication;
    a bedside computing device communicatively linked to said bedside machine through said data port and communicatively linked to a network through a network port; and
    a centralized data repository communicatively linked to said bedside computing device though said network port, wherein said centralized data repository is configured to convert data received from said bedside computing device in a machine-specific format into a machine-independent format based upon a predetermined machine-independent schema and to synchronize the received data with data from at least one other bedside machine, wherein said bedside machines utilize different machine-specific data conventions.

7. The system of claim 6, further comprising a physiologic information system, wherein said physiologic information system is selected from the group consisting of a care network information system, a laboratory information system, and a pharmacy information system.

8. The system of claim 6, further comprising:
    a clinical research information system, wherein at least a portion of said data from said bedside machines is remotely accessible to said clinical research information system.

9. A system for integrating bedside physiologic treatment data comprising:
    at least two bedside machines, each configured to monitor at least one physiological condition, wherein each bedside machine comprises a data port, wherein said bedside machines utilize different data conventions when conveying data via said data ports; and
    a centralized data repository communicatively linked to said bedside machines through the respective data ports of said bedside machines, wherein said centralized data repository is configured to convert data received from said bedside machines into a machine-independent format based upon a predetermined machine-independent schema.

10. The system of claim 9, further comprising:
at least one bedside computing device having at least one bedside machine driver configured for particular ones of said bedside machines to facilitate data exchanges between said bedside machines and said bedside computing device.

11. The system of claim 10, wherein said bedside computing device is configured to communicate said physiologic treatment data with a data source selected from the group consisting of a laboratory information system, a hospital information system, and a pharmacy information system.

12. The system of claim 9, further comprising a machine-specific data store communicatively linked to the centralized data repository and having at least one table for cross-referencing machine-specific data to standardized data.

13. The system of claim 9, further comprising a machine-specific data store communicatively linked to the centralized data repository and having at least one table for cross-referencing database-specific data to standardized data.

14. A machine-readable storage having stored thereon, a computer program having a plurality of code sections, said code sections executable by a machine for causing the machine to perform the steps of:
receiving physiologic treatment data from at least two bedside machines;
converting said physiologic treatment data from a machine specific format into a machine independent format within a computing device remotely located from said bedside machines;
performing at least one programmatic action involving said machine-independent data; and
presenting results from said programmatic actions upon a bedside graphical user interface.

15. The machine-readable storage of claim 14, wherein said converting step further comprises the steps of:
receiving a data stream from each of said bedside machines;
for each data stream, determining a transport protocol for said data stream, wherein said transport protocol is particular to said bedside machine; and
segmenting said data streams into discrete elements.

16. The machine-readable storage of claim 15, further comprising the steps of:
for each of said discrete elements, referencing a data store to determine a standard data format associated with said discrete element; and
converting at least a portion of said discrete elements into said standard data format, wherein said presenting step uses said standard data format.

17. The machine-readable storage of claim 14, further comprising the steps of:
removing patient specific information from said physiologic treatment data; and
storing said physiologic treatment data for clinical research use.

18. The machine-readable storage of claim 14, further comprising the step of:
responding to a request from said bedside graphical user interface in perceptual real-time.

* * * * *